(12) United States Patent
Mark

(10) Patent No.: US 7,193,701 B2
(45) Date of Patent: Mar. 20, 2007

(54) GRAY OPTICAL STANDARD

(76) Inventor: Howard L. Mark, Mark Electronics, 69 Jamie Ct., Suffern, NY (US) 10901

( * ) Notice: Subject to any disclaimer, the term of this patent is extended or adjusted under 35 U.S.C. 154(b) by 104 days.

(21) Appl. No.: 11/193,938

(22) Filed: Jul. 29, 2005

(65) Prior Publication Data

US 2006/0028647 A1  Feb. 9, 2006

Related U.S. Application Data

(60) Provisional application No. 60/599,430, filed on Aug. 6, 2004.

(51) Int. Cl.
*G01J 1/02* (2006.01)

(52) U.S. Cl. .............. 356/243.1; 356/243.5; 250/252.1

(58) Field of Classification Search .. 356/243.1–243.5, 356/432–440; 250/252.1, 343, 353, 338.1, 250/428
See application file for complete search history.

(56) References Cited

U.S. PATENT DOCUMENTS

| | | | | |
|---|---|---|---|---|
| 3,205,355 A | * | 9/1965 | Ehlert | 250/252.1 |
| 3,764,364 A | | 10/1973 | Seiner | 117/18 |
| 4,035,085 A | | 7/1977 | Seiner | 356/179 |
| 4,082,950 A | | 4/1978 | Chen | 250/343 |
| 4,465,929 A | | 8/1984 | Edgar | 250/252.1 |
| 4,647,198 A | * | 3/1987 | Sommer | 356/243.1 |
| 4,761,552 A | | 8/1988 | Rosenthal | 250/252.1 |
| 4,866,644 A | * | 9/1989 | Shenk et al. | 356/319 |
| 4,912,720 A | | 3/1990 | Springsteen | 372/72 |
| 4,969,739 A | | 11/1990 | McGee | 356/308 |
| 5,462,705 A | | 10/1995 | Springsteen | 264/122 |
| 5,488,473 A | | 1/1996 | Springsteen et al. | 356/317 |
| 5,763,519 A | | 6/1998 | Springsteen | 524/403 |
| 5,936,727 A | | 8/1999 | Trygstad | 356/243.5 |
| 5,982,542 A | | 11/1999 | Hannon et al. | 359/559 |
| 2004/0262510 A1 | | 12/2004 | Springsteen et al. | 250/252.1 |

FOREIGN PATENT DOCUMENTS

| EP | 001227312 A1 | * | 7/2002 |
|---|---|---|---|
| JP | 03-146850 | * | 6/1991 |

OTHER PUBLICATIONS

Paul Geladi et al., Hyperspectral imaging: calibration problems and solutions, Jan. 29, 2004, 9 pages, © 2004 Elsevier B.V.

* cited by examiner

*Primary Examiner*—Hoa Q. Pham
(74) *Attorney, Agent, or Firm*—St. Onge Steward Johnston & Reens LLC

(57) ABSTRACT

A system for providing and using a gray optical standard is disclosed, the standard generally comprising a housing having a cavity and an at least partially transparent portion adjacent to the cavity for receiving the radiation emitted radiation by an optical instrument and a particulate material disposed in the cavity. The particulate material is a mixture of highly absorptive and highly reflective particles having a diameter of about 20 microns or less. In some embodiments, the at least partially transparent portion of the housing is modified to be highly diffusely scattering in the wavelength region of interest.

32 Claims, 3 Drawing Sheets

GRAY OPTICAL STANDARD

RELATED APPLICATIONS

This patent application claims the benefit of, under Title 35, United States Code, Section 119(e), U.S. Provisional Patent Application No. 60/599,430, filed Aug. 6, 2004.

FIELD OF THE INVENTION

The present invention relates to providing a gray material used in optical standards. More specifically, the invention relates to a gray optical standard for calibrating analytical instruments.

BACKGROUND OF THE INVENTION

A number of analytical instruments, such as spectrophotometers, are currently available to measure the reflectance of various materials, usually on a wavelength-by-wavelength basis. In principle, reflectance of a material can vary from 0% (black) to 100% (white). However, real materials never really reach these ideal values, and the reflectance range of actual materials typically varies from a low of 1–2% to a high of approximately 99%.

In order to accurately measure absolute reflectance of a test material, the analytical instrument has to be properly calibrated. Although it is possible to use a highly reflective (>90% reflective) standard and a highly absorptive (>90% absorptive) standard, which are readily available, it is not the best way to perform those calculations because the calculated reflectance is subject to errors caused by possible non-linearity of response of the instrument. It is preferable, therefore, to bracket, as closely as possible, the reflectance of the unknown material with calibration standards of known reflectance. The possible non-linearity will have a smaller range in which to act and, therefore, the results can be more accurate. This can be achieved by using standards having reflectance between the ends of the reflectance spectrum, commonly known as "gray" standards.

In order to produce different "gray" standards, it has been suggested to combine materials having various degrees of reflectance, the amount of each dependent on the desired reflectance of the final standard. There are various "gray" standards having a wide range of reflectance available in the marketplace.

However, one problem with these standards is that the materials used to prepare them are not sufficiently homogeneous. For example, some new instrumentation uses imaging microscopes to measure the reflectance spectra of hundreds or thousands of microscopically-sized spots on a sample and thereby determines what has come to be called a "hyperspectral image". Therefore, the use of non-uniform material has resulted in a situation where a nominally "gray" standard is actually resolved into regions with varied reflectance, none of which can be calibrated for their absolute reflectance.

In addition, the presence of unusually light or unusually dark regions in a standard can potentially affect the readings produced by instruments (including older spectrometers) that observe a large area of a sample when high-precision measurements are attempted, due to the light or dark spots moving into or out of the field of view of the instrument.

Another need for a uniformly "gray" standard arises even when absolute reflectance values are not needed. For example, an extremely uniform "gray" standard is essential to characterizing the relative response of different detectors in a multi-detector array.

What is desired, therefore, is a calibration standard formed from "gray" material that is much more homogeneous through the visible and near-infrared regions of the spectrum than the materials currently used. What is also desired is the method for calibrating optical instruments using these standards.

SUMMARY OF THE INVENTION

Accordingly, it is an object of the present invention to provide a calibration standard formed from "gray" material that is much more homogeneous through the visible and near-infrared regions of the spectrum than the materials currently used.

It is a further object of the present invention to provide a method for calibrating optical instruments using these standards.

In order to overcome the deficiencies of the prior art and to achieve at least some of the objects and advantages listed, the invention includes a housing adapted to be mounted in an analytical instrument. The housing comprises at least one portion made of an at least partially transparent material that allows the particulate material contained inside the housing to be exposed to radiation emitted by the optical instrument.

The particulate material is a mixture of highly reflective and highly absorptive particles. The ratio of highly reflective particle to highly absorptive particles is calculated based on the desired wavelength response of the standard. For the purposes of this invention, a highly reflective particle is a particle that reflects at least 90% of radiation in the spectral region of interest. Similarly, a highly absorptive particle is a particle capable of absorptive at least 90% of the radiation in the spectral region of interest.

The particles used for the "gray" material are about 20 microns or less in diameter. Using very small particles as a starting material ensures that the resulting particulate material is homogeneous and cannot be resolved into regions with varied reflectance, none of which can be calibrated for their absolute reflectance. A few commercially available materials satisfy this requirement and will be discussed below.

The ratio of highly reflective particles to highly absorptive particles is calculated based on the desired wavelength-dependent reflectance of the standard. After the calibration standard is manufactured, it can be sent out to a standards laboratory to determine its absolute reflectance. The absolute reflectance can later be used to calibrate analytical instruments or measure the wavelength-dependent reflectance of the test samples.

In some embodiments, the radiation emitted by the optical instrument is diffused by the standard. In certain embodiments, this is achieved by etching a surface of the transparent portion of the housing. In other embodiments, a sheet of material that has no absorbance but is highly diffusively scattering is disposed on at least one of the surfaces of the transparent portion of the housing. In some embodiments, at least a section of the housing is optically diffusing.

Accordingly, in one embodiment, the invention comprises an optical standard for calibration of an analytical instrument, including a housing having a cavity and an at least partially transparent portion adjacent to the cavity for receiving radiation emitted by the instrument, and a particulate material disposed in the cavity, wherein the particulate material comprises a mixture of particles that are at least about 90% absorptive and particles that are at least about 90% reflective, and wherein substantially all of the particles have a diameter of about 20 microns or less.

In another embodiment, the invention comprises a method for calibration of an analytical instrument, including providing an analytical instrument that emits radiation, providing an optical standard having a known wavelength-dependent reflectance, the standard comprising a housing having a cavity and an at least partially transparent portion adjacent to the cavity for receiving the radiation emitted by the instrument, and a particulate material disposed in the cavity, wherein the particulate material comprises a mixture of particles that are at least about 90% absorptive and particles that are at least about 90% reflective, and wherein substantially all of the particles have a diameter of about 20 microns or less, measuring the wavelength-dependent reflectance of the standard, and calculating a relationship between the measured reflectance and the known reflectance of the standard.

In yet another embodiment, the invention comprises a method for testing an analytical instrument, including providing an analytical instrument that emits radiation and includes an array of detectors, providing an optical standard comprising a housing having a cavity and an at least partially transparent portion for receiving the radiation emitted by the instrument, and a particulate material disposed in the cavity, wherein the particulate material comprises a mixture of particles that are at least about 90% absorptive and particles that are at least about 90% reflective, and wherein substantially all of the particles have a diameter of about 20 microns or less, generating a wavelength-dependent reflectance pattern of the standard, and analyzing the pattern to determine the uniformity of the sensitivity of the detectors comprising the array.

DETAILED DESCRIPTION OF THE DRAWINGS

Figure 1:
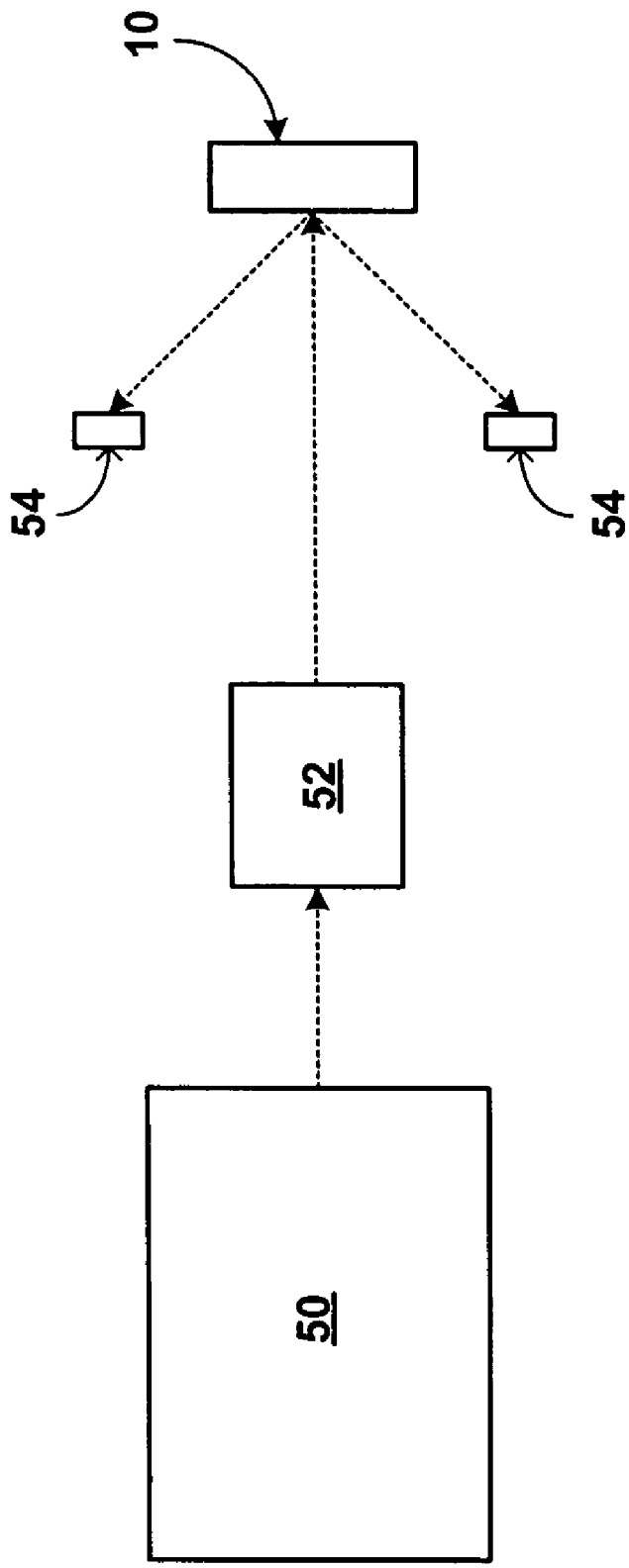
FIG. 1 is schematic view of a system employing an optical standard in accordance with the invention.

The basic components of one embodiment employing a "gray" optical standard in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

A spectrometer 50 typically emits radiation, which passes through some form of optics 52, to an optical standard 10. For example, the spectrometer 50 may receive radiation via an entrance slit (not shown), and subsequently emit the radiation, which passes through exit slit optics 52 to the standard 10. The standard 10, which is located where a test sample would ordinarily be located during sample analysis, reflects the radiation to detectors 54.

Figure 2A:
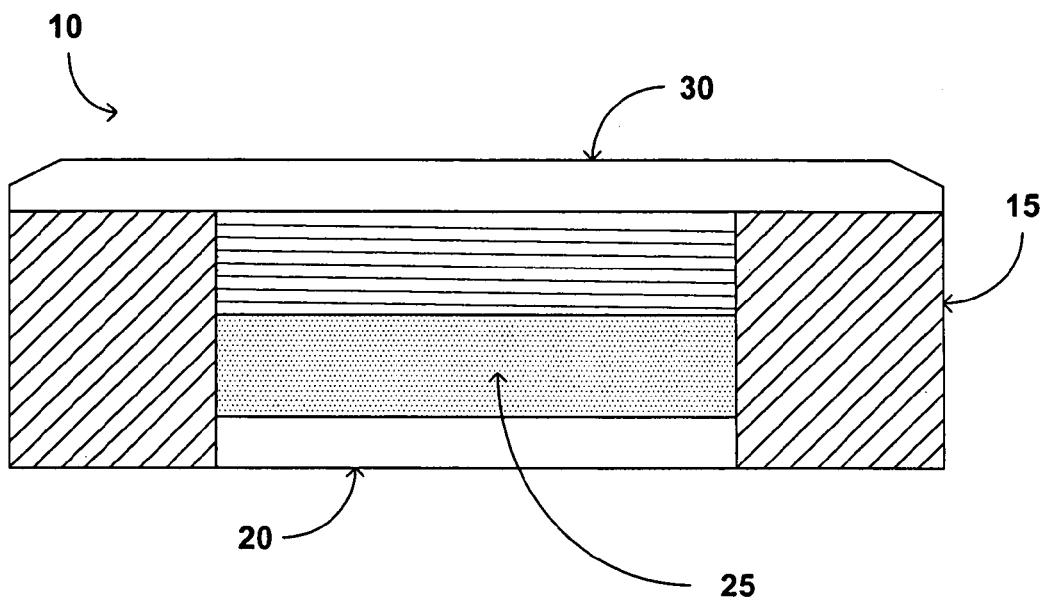
FIG. 2A is cross-sectional view of the optical standard of FIG. 1.

The optical standard 10 includes a housing 15 and a particulate material 25 contained within the housing 10 as shown in FIG. 2A. The housing 15 can be made of any material that can be easily adapted to be mounted in an optical instrument such as wood, plastic or metal.

Figure 2B:
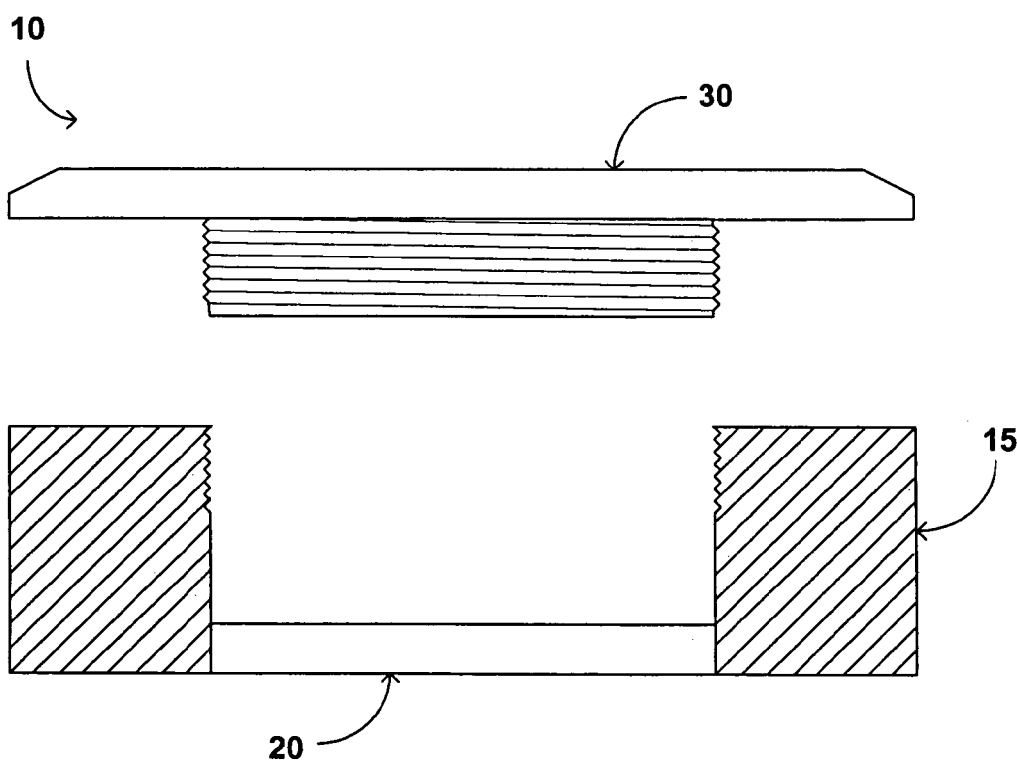
FIG. 2B is an exploded view of the housing of the optical standard of FIG. 1.

As shown in FIG. 2B, the housing 15 has a transparent portion 20, such as a window disposed in one side of the housing. This portion 20 may be comprised of any material that is clear and transparent in the spectral region of interest. Quartz, sapphire, and glass satisfy these requirements in the visible and near infrared regions of the spectrum and, therefore, can be used for the current application as the portion 20.

A lid 30, which may, for example, be made from the same material as the rest of the housing 15, is designed to fit inside the housing 15 in order to seal the particulate material 25 inside a cavity 35. The lid 30 also keeps the surface of particulate material 25 flat against the transparent portion 20, which is important in order to prevent any part of particulate material 25 from casting shadows on any other part.

The particulate material 25 is a mixture of highly reflective and highly absorptive particles. The particles are typically about 20 microns in diameter or less. The use of small particles ensures that the resulting particulate material is homogeneous and cannot be resolved into regions with varied reflectance, none of which can be calibrated for their absolute reflectance.

There are a number of commercially available materials that satisfy the requirements specified above. For example, Fisher Scientific Corporation offers lampblack material that is very highly absorptive and has an average particle size of approximately 0.005 microns. Polymist F5A, a form of powdered polytetrafluoroethylene, is available from Solvay-Solexis Corporation and is a highly reflective material. Another highly reflective material is Algoflon L2003, also a form of powdered polytetrafluoroethylene available from Solvay-Solexis Corporation. These particles have an average size of 6 microns, with 99% of particles being less than 20 microns in diameter. Furthermore, these particles are agglomerations of particles that are approximately 0.2 micrometers, and therefore, de-agglomeration of the individual particles would lead to even greater success.

Wet forms of finely-powdered polytetrafluoroethylene are also commercially available. These are useful for mixing with finely-powdered lampblack (or other black material) in a liquid medium, as will be described below. Examples of such wet preparations of polytetrafluoroethylene are Algoflon 3300 series with an average particle size of 0.22 micrometers and Algoflon D60/A with an average particle size of 0.24 micrometers. Besides polytetrafluoroethylene, particles of such materials as polytetrafluoroethylene, polychlorotriflouroethylene, polychlorofluoroethylene, polyvinyledene fluoride and polyvinyl fluoride, fluoronated ethylene propylene copolymer, perfluoroalkoxy copolymer, polyisopropylidene fluoride, polyvinylidene fluoride, and polychlorofluoroalkenes can also be used.

In order to make a uniform "gray" particulate matter 25, the highly reflective and highly absorptive particles have to be mixed thoroughly to achieve intimate commingling of the particles. Mixing can be done dry or wet. The mixing can be achieved using any well known method that ensures uniform blending of the highly reflective and highly absorptive particles. Examples for suitable mixing processes are described below.

For dry mixing, a powered, mechanical mixer is desirable, in order to aid and speed up the process of intimately commingling the highly absorptive and highly reflective materials. One type of mixer that can be used successfully is one with a rapidly spinning flat blade, commonly known as a "coffee grinder". Two brands and models of coffee grinder have been successfully used to achieve the desired results—a Braun model KSM2 and a Black and Decker model CBG5. Other brands and models will also be satisfactory as long as their blades spin rapidly enough to disperse the powder so the particles can intimately intermingle. For the coffee grinders listed, 30 grams of material should be mixed at a time, although less or more can also be used. While the mixing is proceeding, the mixer should be picked up and shaken vigorously in all directions. The purpose of this is to shake loose any clumps of material that might adhere to the walls of the mixer, which would prevent the material in those clumps from being thoroughly mixed with the rest of the material in the mixer.

Periodically during mixing, the mixer should be stopped. The first reason for stopping the mixer is to examine the particulate mixture to determine if it has reached a state of sufficient uniformity. It may be necessary to examine the mixture under a microscope in order to ascertain this. Preferably, the mixture should be pressed up against a smooth surface (e.g., a flat plate of glass, quartz or sapphire) to avoid shadows that will mask any non-uniformity present.

Another reason to periodically stop mixing is to examine the mixer and the material in it to determine if any of the material is sticking to any part of the mixer chamber and not being commingled with the bulk of material. A small brush should be used to sweep all the powder from the walls, cover and other parts of the mixer into the main mass of material in the central part of the chamber to insure that all material in the mixer is commingled.

Mixing should continue until the material in the mixer is thoroughly mixed and no differences in the appearance of the material are visible even through a microscope.

Alternatively, the particulate material can be prepared using wet mixing, which involves placing the highly absorptive and highly reflective particles, separately or together, into a liquid that will aid in their dispersion. If the materials are dispersed separately, the liquids containing the suspensions should be combined after the materials are dispersed. Vigorous mechanical stirring, either manually or using a powered stirrer, will aid in and speed up the dispersion process.

After the gray particulate material 25 is produced, it can be used to create the standard 10. If the particulate material 25 was prepared by dry mixing it can simply be dispensed into the cavity 35 of the housing 15. The lid 30 is then closed, pressing the particulate material 25 flatly against the inside of the transparent portion 20 and sealing the gray material inside the cavity 35.

If the particulate material 25 was prepared by wet mixing, the material can be dried first. This can be achieved by removing the liquid using any well-known evaporation or sublimation techniques. After the particulate material 25 is dried, it can be ground, if necessary, and then used the same way as the particulate material produced by dry mixing, as described above. Alternatively, the wet material can be poured into the cavity 35 and then dried.

In other embodiments, the wet particulate material is used as the standard. The wet material can be poured inside the cavity 35 and then sealed before the liquid has a chance to evaporate. If the wet material is to be used for a standard, then it is preferable for the liquid not to have absorbance bands in the spectral region in which the gray standard is to be used. Many clear, non-absorbent liquids are available for use in the visible region of the spectrum, including, for instance, water and isopropanol. In the near-infrared region of the spectrum, carbon tetrachloride ($CCl_4$), Freon-11 ($CCl_3F$) and Freon-113 ($CFCl_2CF_2Cl$) are examples of liquids that have no absorbance bands in this spectral region.

Another method to create a standard is to sinter the "gray" particulate material that has been prepared by either dry or wet mixing. Polytetrafluoroethylene has the property that, under suitable conditions of heat and pressure, the particles of a powder will adhere to each other, thus forming a self-supporting piece. A "gray" material containing polytetrafluoroethylene may thus be sintered, to form a block of "gray" material. This block can be adapted to fit into the cavity 35 of the standard housing 15 or can be used as a self-contained standard.

Although the mixing method described produces the particulate material that is satisfactorily uniform for use as an optical standard for calibrating instruments, the calibration standard 10 can be even further improved by providing a housing that includes a diffusing layer. One way this can be achieved is by covering the portion 20 with a sheet of material that has no absorbance in the wavelength region of interest but is highly diffusely scattering. For example, a sheet of polytetrafluoroethylene may be suitable for this purpose in the visible and near-infrared regions of the spectrum. Alternatively, a surface of the transparent portion 20 may be "frosted" by roughening one or both surfaces by, for example, mechanical or chemical etching. In some embodiments, at least a section of the housing is optically diffusing.

Once the "gray" standards are prepared and their absolute reflectance determined, they can be used to calibrate the optical instrument, verify the instrument's linearity over time, check the agreement between two or more instruments, and determine the reflectance of an unknown material. First, the reflectance of two standards with known reflectance is measured by the optical instrument. Then the relationship between the known values and the actual values is calculated in accordance with the following equation:

$$K = \frac{R_{high} - R_{low}}{r_{high} - r_{low}} \quad (1)$$

Where:
K is the relationship between the known and actual values
$R_{high}$ is a known reflectance of the standard with higher reflectance;
$R_{low}$ is a known reflectance of the standard with lower reflectance;
$r_{high}$ is instrument's response to the standard with higher reflectance; and
$r_{low}$ is instrument's response to the standard with lower reflectance.

The calculation of K can be used for any purpose described above. If checking linearity of the instrument over time, Ks calculated at different times can be compared and the instrument can be adjusted if necessary. Similarly, the same standards can be tested on different instruments and their respective Ks can be compared. K can also be used to determine the actual reflectance of a test material, having a reflectance between $R_{high}$ and $R_{low}$, using the following equation:

$$R_{unk} = K(r_{unk} - r_{low}) + R_{low} \quad (2)$$

Where:
K is relationship calculated as described above;
$R_{unk}$ is an actual reflectance of the test material;
$R_{low}$ is a known reflectance of the standard with lower reflectance;
$r_{unk}$ is instrument's response to the test material; and $r_{low}$ is instrument's response to the standard with lower reflectance.

Figure 3:
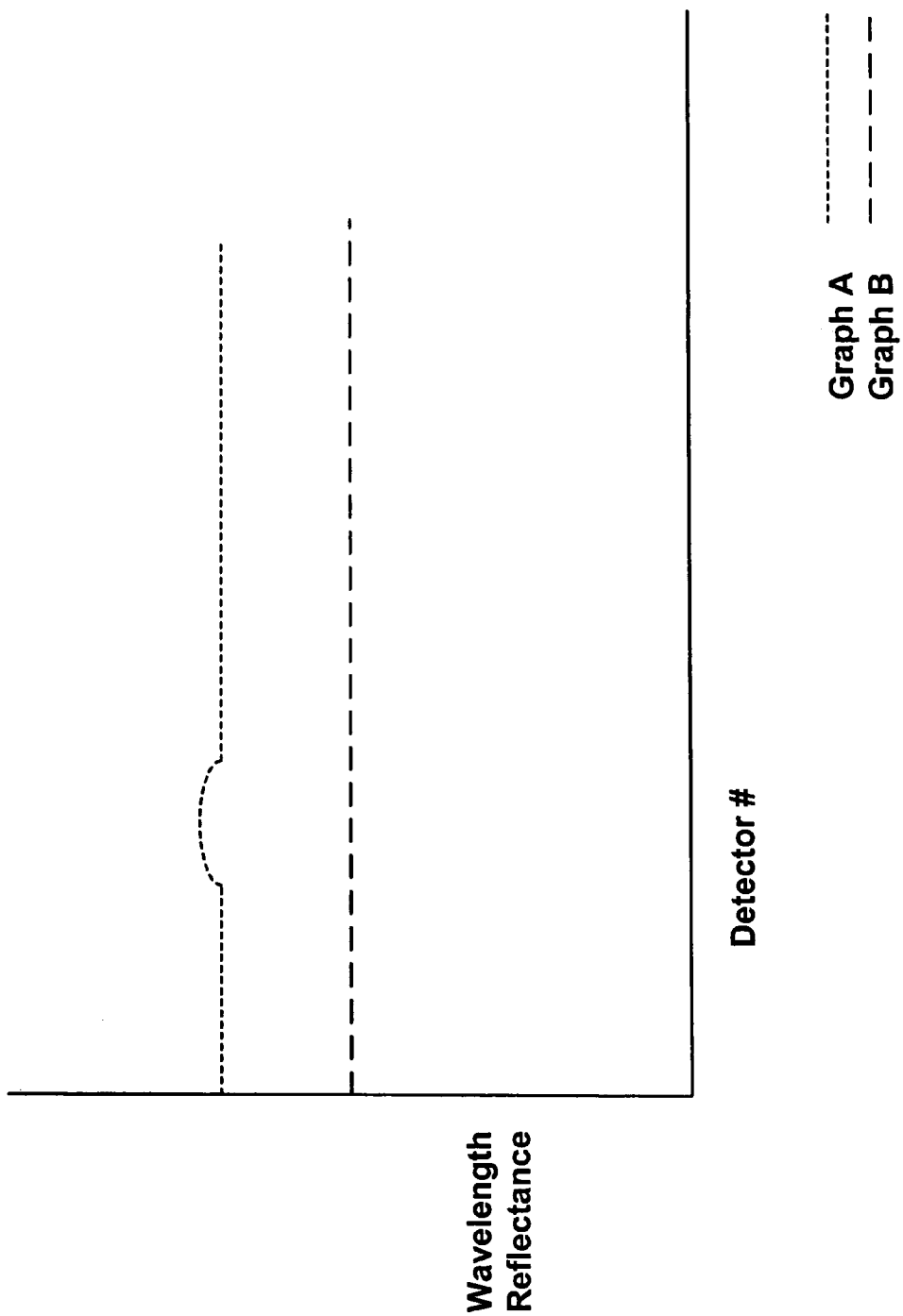
FIG. 3 is plot of uniform and non-uniform responses of detector arrays obtained using the invention of FIG. 1.

The "gray" standards can also be used to verify uniformity of response of individual detectors in a spectrophotometer that utilizes an array of detectors. A non-uniform reflectance pattern may be obtained during tests even when other necessary conditions for obtaining uniform results have been satisfied. Graph A of FIG. 3 demonstrates one possible non-uniform result. When such a response is obtained, it is not always clear whether the non-uniformity is caused by the properties of the test material or by the fact that the individual detectors have non-uniform sensitivity. The uniformity of the individual detectors can be easily checked using the optical standard subject of the present invention. By presenting a uniformly gray field to the instrument, one can test the sensitivity of individual detectors, presuming the other necessary conditions, such as, for example, uniform illumination of the standard, have been satisfied. Since the standard of the present invention is known to be uniform, the non-uniform reflectance pattern obtained using the standard will mean that the detectors have a non-uniform response and vice versa. If a response obtained using the "gray" standard subject of this invention resembles Graph B of FIG. 3, then the detectors have a uniform response.

It should be understood that the foregoing is illustrative and not limiting and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method for calibration of an analytical instrument, the method comprising:
   providing an analytical instrument that emits radiation;
   providing an optical standard having a known wavelength-dependent reflectance, the standard comprising
   a housing having a cavity and an at least partially transparent portion adjacent to the cavity for receiving the radiation emitted by the instrument; and
   a particulate material disposed in the cavity, wherein the particulate material comprises a mixture of particles that are at least about 90% absorptive and particles that are at least about 90% reflective, and wherein substantially all of the particles have a diameter of about 20 microns or less;
   measuring the wavelength-dependent reflectance of the standard; and
   calculating a relationship between the measured reflectance and the known reflectance of the standard.

2. The method of claim 1, further comprising:
   measuring a wavelength-dependent reflectance of a test sample; and
   calculating actual wavelength-dependent reflectance of the test sample using the relationship between the measured reflectance and the known reflectance of the standard.

3. The method of claim 1, further comprising adjusting the instrument based on the relationship between the measured reflectance and the known reflectance of the standard.

4. The method of claim 1, wherein the at least partially transparent portion of the housing is transparent in the visible and near-infrared regions of the electromagnetic spectrum.

5. The method of claim 1, wherein the at least partially transparent portion of the housing includes at least one surface that is etched.

6. The method of claim 1, wherein at least a section of the housing is optically diffusing.

7. The method of claim 1, wherein a sheet of diffusing material is disposed on at least one surface of the at least partially transparent portion of the housing.

8. The method of claim 7, wherein the sheet of diffusing material is a sheet of polytetrafluoroethylene.

9. The method of claim 1, wherein the proportion of the absorptive particles to the reflective particles is selected according to a desired wavelength-dependent reflectance of the standard.

10. The method of claim 1, wherein the absorptive particles comprise lampblack.

11. The method of claim 1, wherein the reflective particles comprise polytetrafluoroethylene.

12. An optical standard for calibration of an analytical instrument, comprising:
   a housing having a cavity and an at least partially transparent portion adjacent to said cavity for receiving radiation emitted by the instrument; and
   a particulate material disposed in said cavity;
   wherein said particulate material comprises a mixture of particles that are at least about 90% absorptive and particles that are at least about 90% reflective; and
   wherein substantially all of said particles have a diameter of about 20 microns or less.

13. The standard of claim 12, wherein said particulate material is wet.

14. The standard of claim 12, wherein said particulate material is dry.

15. The standard of claim 12, wherein the at least partially transparent portion of said housing is transparent in the visible and near-infrared regions of the electromagnetic spectrum.

16. The standard of claim 12, wherein the at least partially transparent portion of said housing includes at least one surface that is etched.

17. The method of claim 12, wherein at least a section of the housing is optically diffusing.

18. The standard of claim 12, wherein a sheet of diffusing material is disposed on at least one surface of the at least partially transparent portion of the housing.

19. The standard of claim 18, wherein said sheet of diffusing material is a sheet of polytetrafluoroethylene.

20. The standard of claim 12, wherein the proportion of the absorptive particles to the reflective particles is selected according to desired wavelength-dependent reflectance of the standard.

21. The standard of claim 12, wherein said absorptive particles comprise lampblack.

22. The standard of claim 12, wherein said reflective particles comprise polytetrafluoroethylene.

23. The standard of claim 12, wherein said reflective particles are selected from the group consisting of polytetrafluoroethylene, polychlorotriflouroethylene, polychlorofluoroethylene, polyvinyledene fluoride and polyvinyl fluoride, fluoronated ethylene propylene copolymer, perfluoroalkoxy copolymer, polyisopropylidene fluoride, polyvinylidene fluoride, and polychlorofluoroalkenes.

24. A method for testing an analytical instrument, the method comprising:
   providing an analytical instrument that emits radiation and includes an array of detectors;

providing an optical standard comprising
- a housing having a cavity and an at least partially transparent portion adjacent to the cavity for receiving the radiation emitted by the instrument; and
- a particulate material disposed in the cavity, wherein the particulate material comprises a mixture of particles that are at least about 90% absorptive and particles that are at least about 90% reflective, and wherein substantially all of the particles have a diameter of about 20 microns or less;

generating a wavelength-dependent reflectance pattern of the standard; and analyzing the pattern to determine the uniformity of the sensitivity of the detectors comprising the array.

25. The method of claim 24, wherein the at least partially transparent portion of the housing is transparent in the visible and near-infrared regions of the electromagnetic spectrum.

26. The method of claim 24, wherein the at least partially transparent portion of the housing includes at least one surface that is etched.

27. The method of claim 24, wherein at least a section of the housing is optically diffusing.

28. The method of claim 24, wherein a sheet of diffusing material is disposed on at least one surface of the partially transparent portion of the housing.

29. The method of claim 28, wherein the sheet of diffusing material is a sheet of polytetrafluoroethylene.

30. The method of claim 24, wherein the proportion of the absorptive particles to the reflective particles is selected according to a desired wavelength-dependent reflectance of the standard.

31. The method of claim 24, wherein the absorptive particles comprises lampblack.

32. The method of claim 24, wherein the reflective particles comprise polytetrafluoroethylene.

* * * * *